United States Patent [19]
Naono

[11] 3,933,436
[45] Jan. 20, 1976

[54] AUTOMATIC ANALYZING APPARATUS
[75] Inventor: Toyohiko Naono, Tokyo, Japan
[73] Assignee: Nihon Denshi Kabushiki Kaisha, Tokyo, Japan
[22] Filed: Aug. 13, 1973
[21] Appl. No.: 387,918

[30] Foreign Application Priority Data
Aug. 15, 1972 Japan................................ 47-81709
Aug. 15, 1972 Japan................................ 47-81715
Aug. 15, 1972 Japan................................ 47-81721
Aug. 15, 1972 Japan................................ 47-95684

[52] U.S. Cl............. 23/253 R; 23/259; 137/625.11
[51] Int. Cl.²................... G01N 33/16; G01N 1/14
[58] Field of Search.......................... 23/253 R, 259

[56] References Cited
UNITED STATES PATENTS
| 3,459,506 | 8/1969 | Finucane........................ 23/253 R X |
| 3,488,154 | 1/1970 | Hronas.......................... 23/253 R X |
| 3,549,330 | 12/1970 | Jungner et al. ............... 23/253 R X |
| 3,557,077 | 1/1971 | Brunfeldt et al................. 23/259 X |
| 3,572,996 | 3/1971 | Reichler et al.................... 23/253 R |
| 3,622,279 | 11/1971 | Moran............................. 23/253 R |
| 3,764,268 | 10/1973 | Kosowsky et al. .............. 23/253 R |
| 3,765,461 | 10/1973 | Keck........................... 23/253 R X |
| 3,832,135 | 8/1974 | Drozdowski et al. ......... 23/253 R X |

Primary Examiner—R. E. Serwin
Attorney, Agent, or Firm—Webb, Burden, Robinson & Webb

[57] ABSTRACT

An analyzing apparatus which automatically and sequentially analyzes a large number and variety of chemical samples which are divided into a plurality of fractions, whereby each sample is simultaneously tested with different chemicals under suitable reaction conditions. The system operates under pressurized closed flow conditions, that is to say, the solution flow lines are compressed with an inert gas, whereby the formation of air bubbles in the flow system, oxidization of samples, reagents, the rise of noxious fumes, are prevented.

3 Claims, 8 Drawing Figures

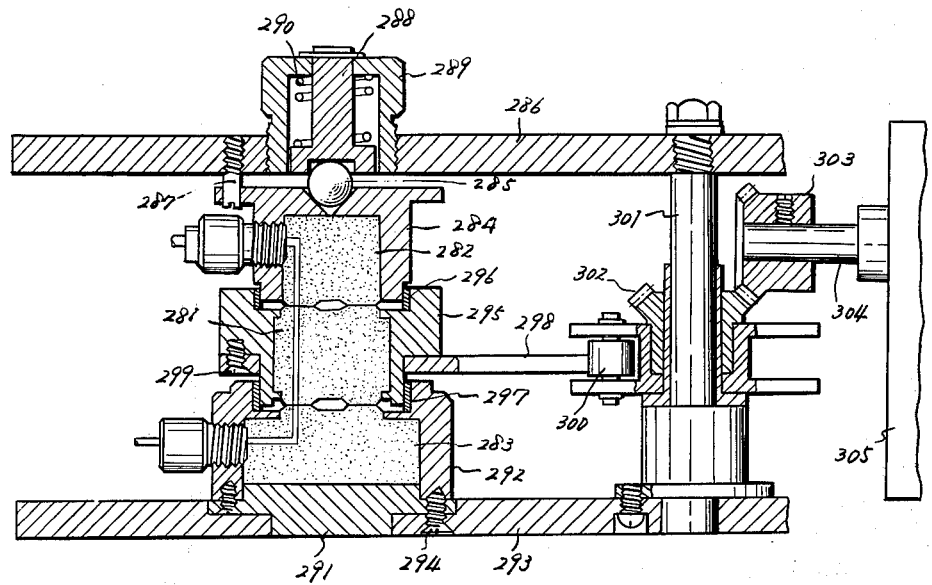
FIG.2
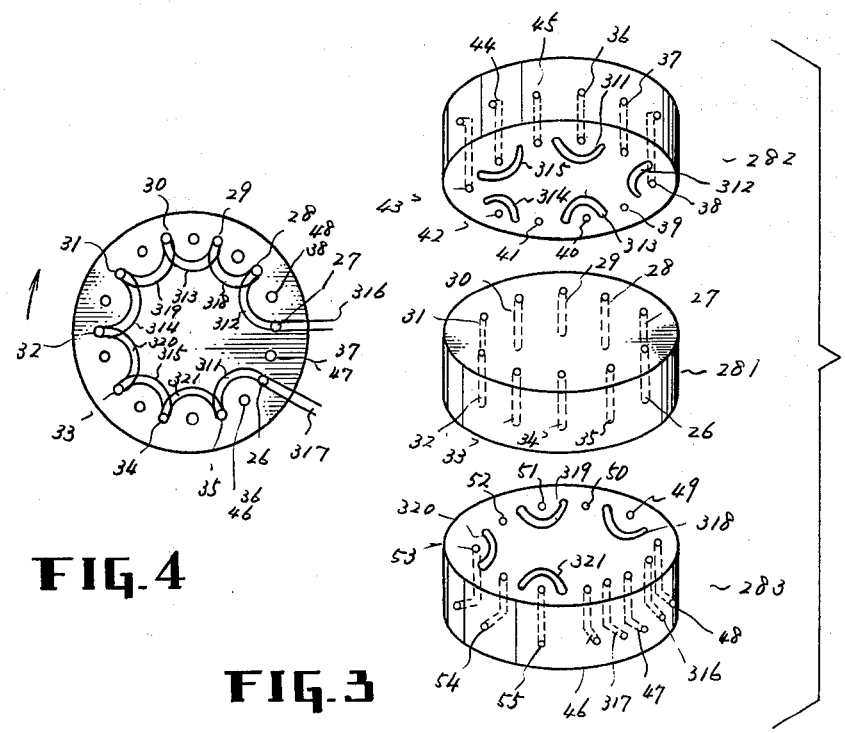
FIG.4
FIG.3

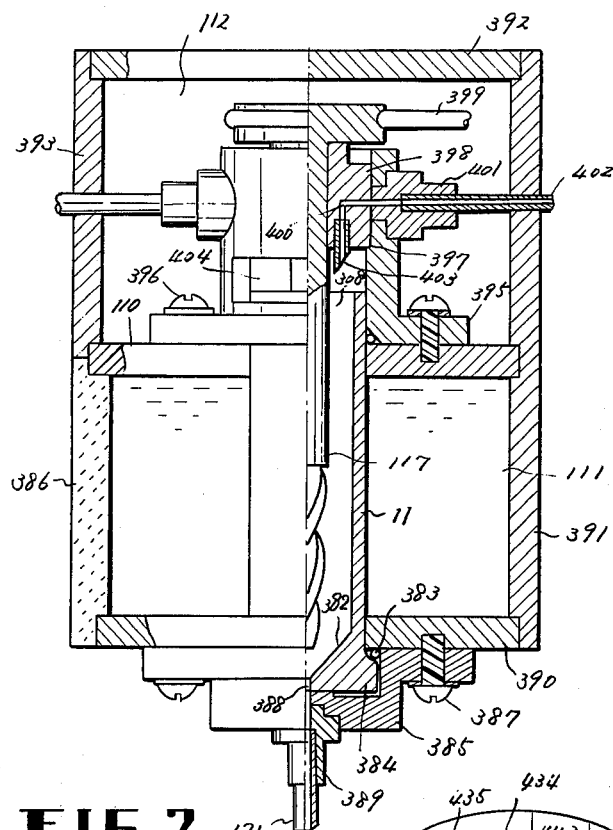
FIG_7
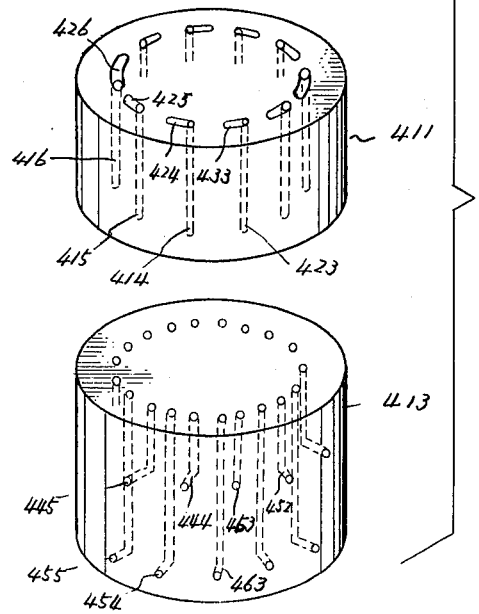
FIG_8

AUTOMATIC ANALYZING APPARATUS

This invention relates to an automatic chemical analyzer suitable for use in clinics, pharmacies and the like.

There has been a growing need in the fields of chemical analysis and medical analysis for an apparatus which can analyze samples like serum repeatedly with high reproducibility and reliability.

However, it has been very difficult to design an apparatus having fully automatic capabilities due to the inherently complicated nature of the operational system involved. But in spite of such difficulties, it was highly desirable to provide a fully integrated system of automation covering such operations as sequential sampling, reagent selection, test type selection, reaction tube selection, flow line washing, etc.; otherwise sequential analysis without cross-contamination of the solutions involved becomes impossible According to this invention there is provided a new automated assay system which satisfies such needs. In particular, it is an apparatus with fully automatic processes that include the measuring of sample volume, feeding of reagent, cleaning of the system, and recording of analytical instrument readout (detection).

An object of this invention is to provide an improved apparatus that automatically and sequentially analyzes fluid samples. Samples may be divided into smaller portions, diluted by a proper diluent or reagent and, afer a chemical reaction, the diluted sample analyzed by a colorimeter or a flame photometer, for example.

Briefly, according to this invention a sequential multi-test system employs a compressed closed flow system; namely, all the sample, reagent and cleaning solution flow lines are pressurized with nitrogen gas and isolated from the atmosphere. The closed system has the following advantages: (a) The pressurized flow lines prevent the formation of air bubbles. (b) Samples and reagent will not oxidize as they are isolated from the air. (c) Being completely closed, the flow lines are free from noxious gas fumes. (d) Analytical mechanisms are simple and durable.

Moreover, the sequential multi-test system according to this invention allows automatic sequential analysis of a plurality of constituents by means of plural channels. With this system, analysis is carried out while automatically changing reagents in sequence. Each time a sample is analyzed, the flow line is cleaned and dried automatically before proceeding with the analysis of the next sample. All operations including data recording may be directed by operation control tape.

These and other objects of the invention will become more readily apparent by reading the following detailed description in conjunction with the accompanying drawings, of which FIG. 1 is a diagrammatic illustration of the apparatus constituting this invention.

FIG. 2 is a cross section of a novel valve construction used in this invention.

FIG. 3 is a projected plan indicating the major section of the sample measuring valve used in FIG. 1.

FIG. 4 is a view of the flow lines of the members shown in FIG. 3.

FIG. 7 is a partial cross-section view of the reaction bath.

FIG. 8 is a projected plan indicating the major section of a waste valve.

THE OVERALL SYSTEM

Figure 1:
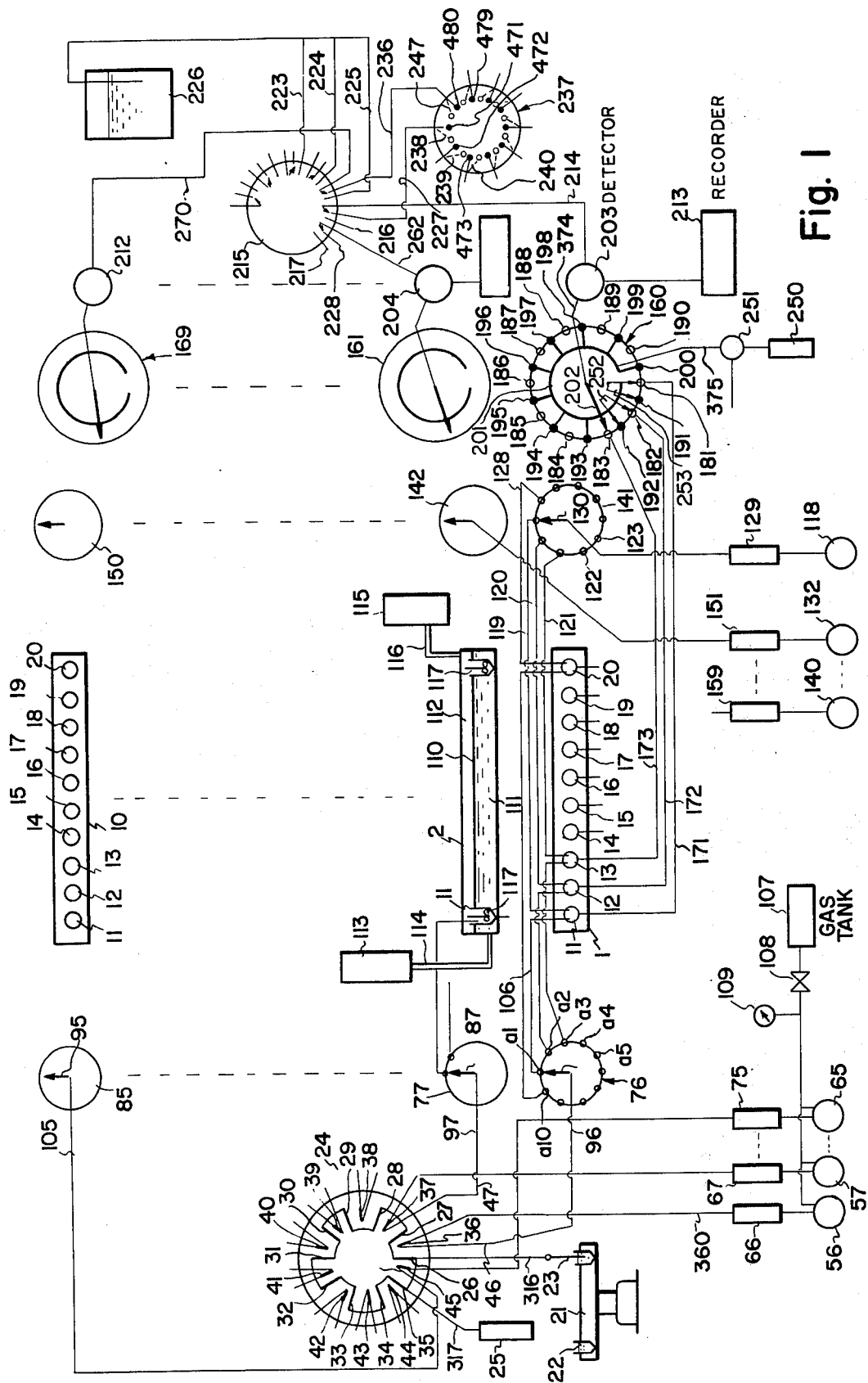

FIG. 1 relates to an embodiment of the invention constructed so that up to ten tests per sample can be simultaneously performed. On reaction bath is provided for each analysis, therefore there are 10 reaction baths 1 – 10, each of which accommodates 10 reaction tubes 11 – 20. (FIG. 1 only shows reaction baths 1, 2 and 10.) This means that the samples of 10 patients can be simultaneously examined with respect to 10 test items. A turntable 21 (actually two turntables are provided) accommodates forty sample tubes 22. Samples such as serum, urine, etc., are placed into sample holding tubes 22 mounted on the said motor-driven turntable 21. The turntable 21 rotates intermittently. Each time the turntable rotates, sample is picked up by a pipette 23 and introduced into a sample measuring valve 24 (its structure will be described in detail later). Sample pickup is achieved by a sample pickup device 25 such as a pump or plunger connected to one of the flow lines of the sample measuring valve 24. The sample measuring valve 24 is designed to draw the sample into ten sample measuring channels 26 – 35 and thus to divide the sample into 10 portions corresponding to the reagents used for testing or the separate tests. After the sample is divided, the sample measuring valve is slightly turned (1/20 of a turn in this embodiment) so that sample measuring channels 26 – 35 will coincide with reagent inlet flow lines 36 – 45 and reagent outlet flow lines 46 – 55 (not all numbered in FIG. 1). The various reagents, water, acetic acid, etc., are contained in reagent reservoirs 56 – 65. (Only reservoirs 56, 57 and 65 are shown in FIG. 1). Reagents preselected according to test items are delivered by constant flow pumps 66 – 75 (66, 67 and 75 shown) into reagent inlet flow lines 36 – 45 to respective sample measuring holes 26 – 35. A gas cylinder 107 containing an inert gas suh as nitrogen or argon pressurizes the reagent reservoirs 56 – 65 and thereby prevent the generation of air bubbles which would impair measurement accuracy. Valve 108 regulates the gas pressure and 109 is a pressure gauge. The reservoirs are pressurized at about 1.5 – 3.0 kg/cm$^2$.

The reagents which are introduced into the sampling valve 24 together with the measured sample fractions are delivered through reagent outlet flow lines 46 – 55 into reaction tube selector valves 76 – 85, respectively (76, 77 and 85 shown). The reagent outlet flow lines 46 – 55 are connected to inlets 86 – 95 of the selector valves 76 – 85 through pipes 96 – 105, respectively (96, 97 and 105 shown). Each reaction tube selector valve is provided with one inlet flow line (86 – 95) and ten direction outlet flow lines $a1 - a10$. For example, mixture of the reagent and sample discharge from outlet flow line $a1$ of the selector valve 76 is injectd through pipe 106 into reaction tube 11 provided in the reaction tube bath 1. A mixture passing through selector valves 77 – 85 is likewise delivered into reaction tubes 11 of the respective reaction baths 2 – 10.

Thus, one sample stored in one sample tube 22 is divided into ten equal portions by the sample measuring valve 24. The ten equal portions of the sample together with the reagent are distributed through their respective selector valves 76 – 85 into the first reaction tube 11 in their respective reaction baths 1 – 10. Then, one sample in the second sample holding tube is likewise divided into ten portions by the sample measuring valve 24, and the ten portions are distributed through their respective selector valves 76 – 85 into the second reaction tube 12 in their reaction baths 1 – 10. Thus after the ten portions of the sample are sequentially measured, they are delivered into the 3rd – 10th reaction tubes. Operation of these valves and pumps is controlled by signals optionally read out from the operation tape.

Each reaction bath (1 – 10) is partitioned by a plate 110 into two compartments. The lower compartment 111 is supplied with a circulation of warm water by a water suppply unit 113 to control the temperature and therefore reaction of the sample. Warm water is thermostatically controlled by warm water piped through pipe 114 from the water supply unit 113. The upper compartment 112 is pressurized with an inert gas such as nitrogen at 1.5 – 3.0 kg/cm$^2$ by a gas cylinder 115 through pipe 116. A reaction tube lies astride both compartments 111 and 112 opening into the upper compartment. The bottom end of the reaction tube is connected to a pipe through which sample is delivered to the analytical instrument (detector) after reaction. A motor-driven stirrer 117 is inserted into the reaction tube to stir the sample and reagent. As reaction tubes 11 – 20 in the respective reaction baths 1 – 10 are filled with samples a reaction reagent contained in a reagent reservoir 118 is fed into the reaction tubes 11 – 20 through flow lines 119 – 128 via pump 129 and passageway 130 of the reagent selector valve 141. Reagent in the reservoirs 132 – 140 are likewise supplied to the reaction tubes 11 – 20 of the respective reaction baths 2 – 10 through reagent selector valves 142 – 150, (only 142 and 150 shown) and pumps 151 – 159 (only 151 and 159 shown) respectively. The reaction reagents are selected according to analysis, such as methanol and acetic acid.

The sample and reagent in each of the reaction tubes 11 – 20 of the respective reaction baths 1 – 10 are stirred by the stirrer 117, and after the lapse of the reaction time, it is delivered into a reaction solution selector valve 160 through pipes 171 – 180 (only 171, 172 and 173 shown).

The reaction solution selector valve 160 is provided with passageways 181 – 190 (shown as open circles on FIG. 1) which are connected to the said pipes 171 – 180. Cleaning flow lines (shown as black dots on FIG. 1) 191 – 200 are speced radially among the said passageways 181 – 190. A loop flow line 201 is connected to the said cleaning flow lines 191 – 200. A distribution duct 202 is arranged for selecting the said passageways 181 – 190 (the structure will be described in detail with reference to FIG. 3). The connections of reaction solution selector valves 161 – 169 corresponding to the 2nd to the 10th reaction baths are the same as described above for valve 160.

The reaction solution selector valves 160 – 169 (160, 161 and 169 shown) are connected to analytical instruments (detectors) 203 – 212 (only 203, 204 and 212 are shown) including a colorimeter respectively. Each time a reaction solution selector valve 160 makes 1/20 of a turn, the reaction solution in reaction tubes 11 – 20 is directed to detector 203 in order, the detection signal of which is recorded by a recorder 213. After detection, the reaction solution passes through pipe 214 into the first waste valve 215.

The first waste valve is equipped with flow lines 216 – 225 (not all shown) connecting to a waste reservoir 226 and flow lines 227 – 236 (not all shown) connecting to the second waste valve 237. The flow lines 262 – 270 are connected to the 2nd to the 10th detectors (204 – 212), respectively. The rotation (1/20 of a turn) of the said second waste valve 237 exposes flow lines 227 – 236 to the air, or alternately isolates them from the air.

DETECTION FLOW LINE CLEANING SYSTEM

Next, cleaning of the reaction tube and the detector flow line will be described. In FIG. 1, when a pipe 173 of the reaction tube 13 in the reaction bath 1 is connected with a duct 202 of the reaction solution selector valve 160, a sample in the reaction tube 13 is forced out by nitrogen gas from a pressure cylinder 115 and is delivered through pipes 173 and 374 into the detector 203. At this time, the first waste valve 215 is connected with the seocnd waste valve 237 which is isolated from the air (closed) (this will be described in detail with regard to FIG. 8), thereby the liquid sample is sent through the pipe 214 and the first waste valve 215 to the second waste valve 237.

After detection or analysis, the reaction solution selector valve 160 makes 1/20 of a turn to block the reaction tube and the detector flow line. By the rotation of valve 160, the duct 202 is connected to the cleaning flow line 193 and the passageways 252 and 253 (see FIG. 6) ae connected to the cleaning flow line 183 and passageway 192 and cleaning flow line 182 and passageway 191, respectively. After the second waste valve is released, the detected sample in the pipe 227 is discharged. Next, the first waste valve 215 is rotated 1/20 of a turn and thereby is connected with a waste reservoir 226. At the same time, a cleaning solution such as the alkaline solution in a cleaning solution reservoir 250 from the cleaning solution pump 251 is delivered through a reaction solution selector valve 160, passageways 252 and 253, pipes 173 and 172 into reaction tubes 13 and 12 and through a detector 203 through flow lines 193 and 202. After the cleaning solution cleans the detector 203, it is discharged through the first waste valve 215 into the waste reservoir 226. The cleaning solution back washes into the reaction tubes and spills into the upper section of the reaction bath from which it is drained.

Thus, the interlocking selector valves feed samples successively into detectors and clean the empty reaction tubes and detectors.

VALVE ASSEMBLY

FIG. 2 is a cross section view of one embodiment of the novel valves useful in applicant's invention. A rotary slide member 281, upper fixed member 282 and lower fixed member 283 are made of borosilicate glass, polytetrafluoroethylene, artificial ruby, etc., making them resist to all erosive organic and inorganic substances. Upper fixed member 282 is supported by a cylindrical framework 284, the center of which is equipped with a conical groove to receive a steel ball 285. An upper base plate 286 is equipped with a removable screwed cylinder 289 and the said steel ball 285 is pressed by a pressure rod 288 which is supported by the cylinder 289. A coil spring 290 is used for biasing the said pressure rod 288 against steel ball 285. Lower fixed member 283 is supported by framework 291 and 292. The framework 291 is clamped down to a plate 293 by a screw 294. The framework 295 supports the rotary member 281. Antisolvent bushings 296 and 297 are provided on the surfaces of frameworks 284 and 292 which are in contact with a framework 295 to maintain axial alinement of the rotary slide member 281 with fixed members 282 and 283 and to enable the rotary member to rotate smoothly. In the framework 295 Geneva gear 298 is held by screws 299 to allow the rotary member to rotate. Said Geneva gear engages intermittently with a roller 300 supported by a support shaft 301. A bevel gear 302 supported by support shaft 301, engages with a bevel gear 303 which is locked on a drive shaft 304 of a motor 305 and the said gear transmits the power of the motor 305 to the Geneva gear 298, rotating the rotary member 281 to change the valve positions. The motor is intermittently driven by limit switches.

SAMPLE MEASURING VALVE

FIG. 3 is an exploded view of the flow directing sample measuring valve 24 shown in FIG. 1: The rotary slide member 281, the upper fixed member 282 and the lower fixed member 283.

Elements in FIG. 3 carry the same numbers as their respective elements in the other drawings. The said members 281, 282, and 283 are alined and moved relative to each other by an assembly such as described with reference to FIG. 2. In the rotary member 281, ten sample measuring holes 26 - 35 are radially spaced. The upper fixed member 282 is equipped with radially spaced reagent inlet flow lines 36 - 45 of the same number as the rotary member 281 and with five grooves 311 - 315 astride reagent inlet flow lines 36, 38, 40, 42 and 44. The said lower fixed member 283 is equipped with radially spaced reagent outlet flow lines 46 - 55 of the same number as the said sample measuring holes in rotary slide 281 and with one flow line; for example, a sample inlet flow line 316 and a sample suction flow line 317 astride a flow line 47. Furthermore, grooves 318 - 321 are engraved astride flow lines 49, 51, 53 and 55 on the surface of the lower fixed member 283 which is in contact with said rotary member 281. The sample inlet flow line 316 is connected to the reagent reservoir and the sample suction flow line 317 connects to the sample suction pump 25.

FIG. 4 shows the positions of the flow lines and grooves of the sample measuring valve in FIG. 3, when the sample volume is measured. The reagent inlet flow lines 36 - 45 of the upper fixed member 282 coincide with the reagent outlet flow lines 46 - 55 of the lower fixed member 283, respectively. When the sample measuring holes 26 - 35 are positioned between the reagent outlet flow lines 45 - 55, one (27 in this figure) of the sample measuring holes 26 - 35 coincides with the sample inlet flow line 316, and the hole 27 coincides with a sample suction flow line 317. A sample from the sample inlet flow line 316 passes through the sample measuring hole 27 and reaches the next sample measuring hole 28 via groove 312 of the upper fixed member 282. Then, the sample is guided through groove 318 of the lower fixed member into the sample mesuring hole 29. Thus, the sample proceeds through the grooves of the upper fixed member and the lower fixed member successively until it finally reaches sample suction flow line 317 through sample measuring hole 26. Then, the rotary member 281 is given 1/20 of a turn in the direction of the arrow with each sample measuring hole loaded with sample. The holes 26 - 35 are shifted to the positions of the reagent inlet flow lines 36 - 45, respectively. As a result, samples measured out in their volume measuring holes together with reagents in the reagent reservoirs 56 - 65 are guided through reagent outlet flow lines 45 - 55 into their respective selector valves 76 - 85. After the sample is discharged from the sample volume measuring hole, the rotary member 281 is given 1/20 of a turn and the sample measuring holes are cleaned.

CLEANING SYSTEM OF THE SAMPLE MEASURING VALVE

Figure 5:
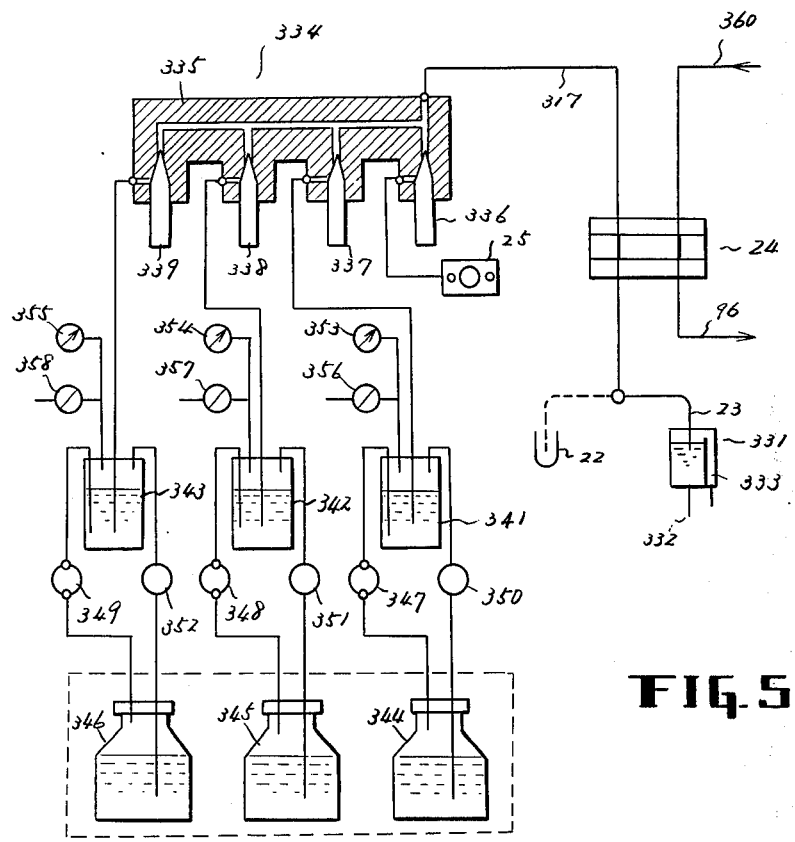
FIG. 5 shows a sample measuring valve cleaning system.

FIG. 5 is a flow line of the sample measuring valve cleaning system. Cleaning of the sample measuring valve 24 is achieved after a sample is injected and delivered into the reaction tube. In the FIGS., 23 and 331 are the sample tube and the cleaning solution reservoir, respectively. The water supply tube 332 feeds water continuously. Surplus water drains off from the right space 333 through drain pipe. A sample suction pipe 23 is constructed so that it can shuttle between the sample tube 22 and the cleaning solution reservoir 331.

The needle valve 334 consists of a needle valve block 335 and plungers 336 - 339. The needle valve is connected to a constant flow pump 25. Sealed vessels 341, 342 and 343 which are pressurized by an inert gas from a gas cylinder (not shown), are filled with cleaning solution, tap water and distilled water pumped from reservoirs 344, 345 and 346. Constant pressure valves 347, 348 and 349 allow the cleaning solution to return through the lines into the reservoirs 344, 345 and 346 when pressure in the sealed vessels 341, 342 and 343 exceeds a given level after supply pumps 350, 351 and 352 have delivered the solution. Pressure gauges 353, 354 and 355 indicate pressure in the sealed vessels and switching valves 356, 357 and 358 are used for drainage.

In this structure, when a plunger 337 is opened, pressure in the sealed vessel 341 forces the cleaning solution through the needle valve 334, through the sample measuring valve 24 and the sample suction tube 23 and into the cleaning solution reservoir 332, thereby cleaning the sample measuring flow lines.

Next, if the plunger 337 is closed and the plunger 338 is opened, the tap water in the closed vessel 342 flows in the same flow lines and drains off all the cleaning solution. Furthermore, when the plunger 338 is closed and the plunger 339 is opened, the distilled water in the closed vessel 343 flows to clean the flow lines completely; then the plunger 39 is closed. After the sample suction tube 23 is moved from the cleaning reservoir 331 into the sample tube 22 as in the dotted line, the plunger 336 is opened and the constant flow pump 25 is operated to draw up a sample in the sample tube 22. On this occasion, the sample is drawn up but not to the extent that the sample tip reaches the needle valve block 335. Then the plunger 336 is closed, the rotor 281 of the sample measuring valve 24 is rotated by 18° (see FIG. 4), a given quantity of reagent in the sample measuring hole 26 is delivered from a supply tube 360, and a given quantity of sample is fed through supply tube 96 and selector valve 76 into the reaction tube 11. The samples in the respective sample measuring holes 27 - 35 likewise transferred into the reaction tubes 11 of the respective reaction baths 2 - 10.

By repeating this sequence, various samples can be successively analyzed. A routine technique is capable of automatically controlling with ease all the operations of the plungers 336 – 339, constant flow pump 25, sample suction tube 23, and the sample measuring valve 24 as well as the supplying of the reagent solution by a programmer.

REACTION SOLUTION SELECTOR VALVE

Figure 6:
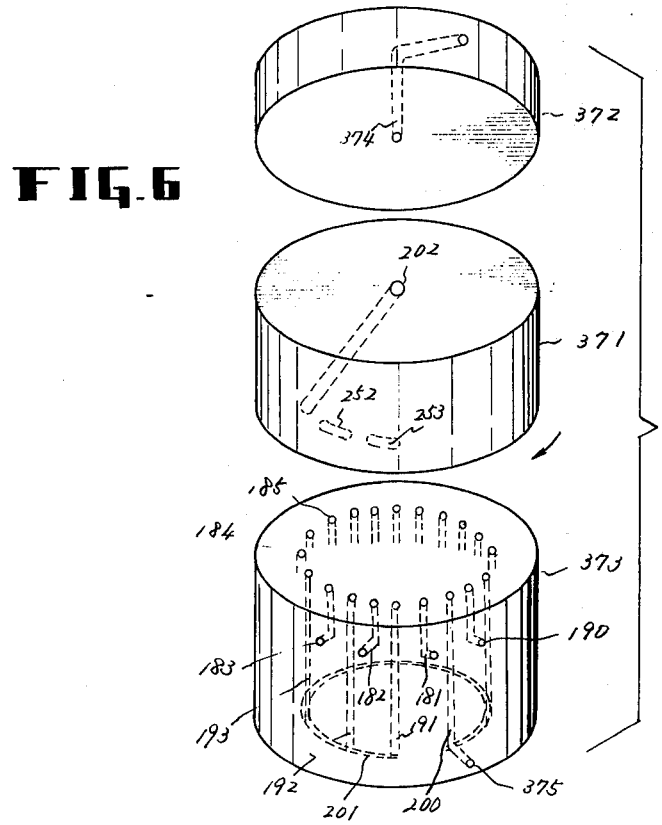
FIG. 6 is a projected plan indicating the major section of a reaction solution selection valve used in this invention.

FIG. 6 is a projected plan indicating the major section of reaction solution selector valve 160 used in FIG. 1. FIG. 6 shows only the rotary member 371 and the upper and the lower fixed members 372 and 373, which can be supported and rotated with the same structure as that of the valve shown in FIG. 2. The rotary member 371 is equipped with an oblique duct 202 one exit of which passes through the rotary center and two grooves 252 and 253 on the surface in contact with the lower fixed member 373. The upper fixed member 372 is equipped with an axially positioned flow line 374 one end of which is connected to the detector 203. The lower fixed member 373 is equipped with flow lines 181 – 190 connected to reaction tubes 11 – 20 at equidistant radially spaced intervals over a circle, and in addition there are cleaning solution flow lines 191 – 200 between the said flow lines 181 – 190. The flow lines 191 – 200 are connected to each other by a loop flow line 201 except between the flow lines 191 and 200. Grooves 252 and 253 engraved in the said rotary member are long enough to connect two adjoining flow lines (for example, 182 and 192).

When, for example, duct 202 in the rotary member 371 connects to the flow line 183 of the lower fixed member 373, a reaction solution in the reaction tube 13 passes through a pipe 173, duct 202, and a flow line 374 of the upper fixed member 372 into the detector 203, where the sample solution is detected. On this occasion, the grooves 252 and 253 in the rotary member 371 coincide with flow lines 182 and 192 and 191 and 181, respectively. The reaction tube is always cleaned by a cleaning system similar to that for the sample measuring valve 24 shown in FIG. 1. Since a cleaning solution is always delivered from the cleaning solution supply pump 251 into loop flow line 201 through pipe 375 (see FIG. 1), the solution proceeds to the grooves 252 and 253 through the flow lines 192 and 191 and it is guided into the flow lines 182 and 181. Then, it passes through pipes 171 and 172, cleaning reaction tubes 11 and 12. When the rotary member 371 makes 1/20 of a turn in the direction of the arrow and the flow line 202 is coincident with a flow line 193 of the lower fixed member 373, the cleaning solution flows into the detector 203 through flow line 201, flow lines 193, 202 and 374, and grooves 252 and 253 coincide with flow lines 183 and 192 and 182 and 191. As a result, reaction tubes 12 and 13 are cleaned.

REACTION BATH

Referring now to FIG. 7, the major elements of the reaction bath 1 are described. The reaction tube 11 is a cylinder with an open top and a funnel-shaped bottom end 382. The reaction bath 1 is formed by plates 390, 391, 392 and 393 defining an enclosure. A plate 110 divides the enclosure into two compartments, namely the pressurized chamber 112 and the water bath 111. The reaction process is directly observed through the observation window 386. An O-ring 383 positioned at a ring convex 384 on the periphery near the base and a push-up member 385 for the reaction tube 11 held down onto the base plate 390 by screws 387 serve to keep the reaction tube 11 and the base plate 386 airtight.

A hole 388 in the center of the funnel-shaped base 384 of the reaction tube 11 leads via a connector 389 into a supply tube 171 connecting to a valve 160 (see FIG. 1). On the other hand, the upper section of the reaction tube 11 is locked by a partitioned panel 110 and a flange pipe-like fixture member 395 clamped by screws 396. In the center of the internal surface of the fixture member 395 there is a step 397 on which a column member 398 is positioned. The column member 398 not only acts as a bearing for the stirrer 117 rotated by a belt 399 but has an opening 400 connecting via a connector 401 to a sample or reagent supply tube 402 and injects the solution via a nozzle 403 into the reaction tube 11. The fixture member 395 has a window 404 which allows the cleaning solution for the reaction tube 11 to flow out into the upper compartment 112.

WASTE VALVE

FIG. 8 illustrates one embodiment of the waste valve 215 shown in FIG. 1, which consists of a rotary slide member 411, upper fixed member 412 and lower fixed member 413. These members are made of borosilic acid glass, ethylene-tetrafluoride resin, ruby, etc. which resist all erosive organic and inorganic substances. The rotary member 411 is equipped with flow lines 414 – 423 radially spaced over a concentric circle and with grooves 424 – 433 on the surface in contact with the upper fixed member 412. One end of each groove coincides with each of the said flow lines 414 – 423 and the other end extends circumferentially halfway toward the adjacent flow line. The upper fixed member 412 is equipped with flow lines 434 – 443 of the same number of the said flow lines 414 – 423 over a concentric circle. The lower fixed member 413 is equipped with the first group of flow lines 444 – 453 connecting to the waste reservoir 226 and the second group of flow lines 454 – 463 connecting to the second waste valve 237 (see FIG. 1). The flow lines 434 – 443 are connected to the detectors 203 – 212, the flow lines 444 – 453 are connected to the waste reservoir 226 and the flow lines 454 – 463 are connected to the second waste valve 237 through flow lines 227 – 236 respectively.

When the sample solution is detected by the detector 203, the flow lines 434 – 443 of the upper fixed member 412 are connected to flow lines 454 – 463 of the lower fixed member 413 through flow lines 414 – 423. At this time, the pipes 227 – 236 are connected to the flow lines 471 – 480 of the second waste valve 237 and isolated from the air. After the detection, the first and second waste valves 215 and 237 are rotated 1/20 of a turn, respectively. Then, the flow lines 434 – 443 of the first waste valve 215 are connected to flow lines 454 – 463 through flow lines 414 – 423, and the rotation of the said second waste valve 237 exposes pipes 227 – 236 to the air. Therefore, residual solution in the pipes 227 – 236 is wasted from flow lines 238 – 247 of the second waste valve 237 and, residual solution in the pipes between the detectors and first waste valve 215 is discharged by the cleaning solution supplied from the pump 250, into the waste reservoir 226 through first waste valve 215 and pipes 216 – 225. With this waste system, drops in the flow line pressure can be prevented, since the cleaning of detectors is completed under the condition that flow lines are isolated from the air.

As described in detail hereinabove, this invention provides an automatical sequential analyzing apparatus of multiconstituents of many samples. If all operations of the automated assay system based on the invention are programmed in advance, all procedures except arrangement of samples can be achieved fully automatically. Moreover, diagnostic data on the patient's samples can be obtained by connecting this system to an on-line computer which processes signals from a detector.

While I have described certain presently preferred embodiments of my invention, it is to be understood that it may be otherwise embodied within the scope of the appended claims.

I claim:

1. An automatic analyzing apparatus comprising:
    a. a plurality of reaction baths corresponding to selectable reaction treatments or conditions, said baths divided by a partition plate into upper and lower chambers, means for circulating a heated fluid in the lower chambers to maintain a constant temperature, and means connecting the upper chambers to an inert gas source to pressurize said upper chambers;
    b. a plurality of reaction tubes, housed in each reaction bath and supported by said partition to open into said upper chambers;
    c. means for drawing sample;
    d. means for dividing the drawn sample into a given number of portions;
    e. means for distributing the divided sample portions, each to a reaction tube in each reaction bath;
    f. means for supplying reagents to the reaction tubes comprising reagent reservoirs, which are closed, and means for supplying compressed inert gas to said reservoirs in order to supply reagent to said reaction tubes;
    g. means for sequentially feeding contents from reaction tubes in each reaction bath to an analyzer associated with said bath; and,
    h. means for backwashing a cleansing solution into said reaction tubes via said means for sequentially feeding contents from reaction tubes to said analyzer.

2. An apparatus according to claim 1 wherein said means for drawing and dividing the sample further include:
    a. a sample suction tube for drawing sample to be analyzed, means for moving said sample suction tube back and forth between sample tubes containing sample and a cleaning solution reservoir;
    b. a sample measuring valve for measuring and fractionating a given quantity of sample drawn by said sample suction tube;
    c. a constant flow pump for drawing a sample via said sample measuring valve and suction tube; and,
    d. means for backwashing a cleaning solution into said cleaning solution reservoir by passing the solution through the said sample measuring valve and said sample suction tube.

3. An apparatus according to claim 1 wherein said means for sequentially feeding and means for backwashing further include:
    a. one or more cleaning solution sources connected to a common delivery means;
    b. a waste reservoir;
    c. a waste valve system for directing flow from the analyzers to the waste reservoir or for sealing the analyzers;
    d. a reaction solution selection valve for sequentially feeding the contents of said reaction tubes to said analyzers comprising:
        i. means for connecting the cleaning solution delivery means to the reaction tubes, the contents of which have been previously delivered to the analyzer in order to backwash cleaning solution through said reaction tube to said waste reservoir; and,
        ii. means for connecting the cleaning solution delivery means to the analyzers after every analysis to wash cleaning solution through said waste valve system to said waste reservoir.

* * * * *

UNITED STATES PATENT OFFICE
CERTIFICATE OF CORRECTION

PATENT NO. : 3,933,436
DATED : January 20, 1976
INVENTOR(S) : Toyohiko Naono

It is certified that error appears in the above-identified patent and that said Letters Patent are hereby corrected as shown below:

Column 2 Line 9 "On" should read --One--.
Column 2 Line 41 "suh" should read --such--.
Column 3 Line 50 "speced" should read --spaced--.
Column 4 Line 30 "ae" should read --are--.
Column 5 Line 53 "45-55" should read --46-55--.
Column 6 Line 5 "45-55" should read --46-55--.
Column 6 Line 50 "39" should read --339--.

Signed and Sealed this twenty-fifth Day of May 1976

[SEAL]

Attest:

RUTH C. MASON
Attesting Officer

C. MARSHALL DANN
Commissioner of Patents and Trademarks